United States Patent
Biet et al.

(10) Patent No.: US 6,528,285 B1
(45) Date of Patent: Mar. 4, 2003

(54) NON RCR LEUCONOSTOC PLASMID CAPABLE OF BEING TRANSFERRED INTO LACTIC ACID BACTERIA, USE AS CLONING AND EXPRESSING TOOL

(75) Inventors: Franck Biet, Colombelle (FR); Yves Cenatiempo, Saint Julien l'Ars (FR); Christophe Fremaux, Poitiers (FR)

(73) Assignee: Texel, St. Romain (FR)

( * ) Notice: Subject to any disclaimer, the term of this patent is extended or adjusted under 35 U.S.C. 154(b) by 0 days.

(21) Appl. No.: 09/530,903

(22) PCT Filed: Nov. 2, 1998

(86) PCT No.: PCT/FR98/02341

§ 371 (c)(1),
(2), (4) Date: Sep. 18, 2000

(87) PCT Pub. No.: WO99/24591

PCT Pub. Date: May 20, 1999

(30) Foreign Application Priority Data

Nov. 6, 1997 (FR) .............................. 97 13977

(51) Int. Cl.⁷ .............................................. C12P 21/06
(52) U.S. Cl. ................ 435/69.1; 435/320.1; 435/252.3; 435/252.9; 536/23.1; 536/24.2
(58) Field of Search ............................ 435/320.1, 252.3, 435/6, 69.1, 252.1; 536/23.1, 23.2, 23.7, 24.2

(56) References Cited

FOREIGN PATENT DOCUMENTS

| WO | 94 06917 | 3/1994 |
| WO | 94 16086 | 7/1994 |

OTHER PUBLICATIONS

Benachour A. et al, "pUCL287 plasmid from Tetragenococcus halophila (Pediococcus halophilus) ATCC 33315 represents a new theta–type replicon family of lactic acid bacteria." FEMS Microbiol Lett, May 1, 1995, 128 (2) pp. 167–75, Netherlands.

Frere J. et al, "Molecular analysis of the Lactococcus lactis subspecies lactis CNRZ270 bidirectional theta replicating lactose plasmid pUCL22." Mol Microbiol, Dec. 1993, 10 (5) pp. 1113–24, England, citied in the application, see the whole document.

Kiewiet R. et al, "Theta replication of the lactococcal plasmid pWV02", Mol. Microbiol, Oct. 1993, 10(2) pp. 319–27.

Benachour A. et al, "pUCL287 plasmid from Tetragenococcus halophila (Pediococcus halophilus) ATCC 33315 represents a new theta–type replicon family of lactic acid bacteria." Fems Micorbiol Lett, May 1, 1995, 128 (2) P167–75, Netherlands.

Frere J. et al, "Molecular analysis of the Lactococcus lactis subspecies lactis CNRZ270 bidirectional theta replicating lactose plasmid pUCL22." MOL Microbiol, Dec. 1993, 10 (5) P1113–24, England, cited in the application, see the whole document.

Kiewiet R. et al, "Theta replication of the lactococcal plasmid pWV02", Mol. Microbiol, Oct. 1993, 10 (2) P319–27,.

Primary Examiner—Ponnathapu Achutamurthy
Assistant Examiner—Kathleen M Kerr
(74) Attorney, Agent, or Firm—Burns, Doane, Swecker & Mathis, L.L.P.

(57) ABSTRACT

The invention concerns a plasmid having a replication mode which is not of the RCR type, and capable of being transferred in stable form into host lactic acid bacteria belonging at least to three different kinds.

25 Claims, 4 Drawing Sheets

```
                Sal1
    1 TCGACGTTAAAAGTTTCCATTCTGTATCTGTGAATGACTTTTTAGATAAATCTATATTAA

61 GGCGTTTAGCTTTCTATTTAAGGCTTGACGTGATATTTCTAGTTCGTCTGCTATCGCGAT

─────────→   IR1      <-
  121 AATGGTATCAAATTCGTGTGTCATCAGTCTCTCCAAACGTAAACTGAAGTGATGTAAAGT
      ──────────
  181 TTACGTTTTAAGTTTACTATATTGCTGACGTTTTAAGTAGGTCATTTAATTATTAAAACA

---DR1---->               ---DR1---->
  241 TAAGATTATTTGTTTGTTTATTGTCATGTATAGTTCTTAATGCTATACTCATATCAACAT
                            ↓
  301 TTAAATACAAATAAAAAGACCTCAACTCTTGCAGGAGTTAGGACTTGGTGACCTAGATAT

EcoRI
  361 TAACACTATCAGGGTTTTGCCATTACAGAATTCGACCTCTGAAATGGCTTAGAATACTTA

421 CTATTATACAAACTTATAGACTAAGAGTAAACAGCTTTACTCAAAAAAGAACTATAAAC

─────────→    IR2           ←─────────
  481 GACTATGAAAGCGTATCCTCCAGCCTAACTAAGCACGAGGATACGCTTTTTACGTCTGTT

----DR2----->
  541 AAGTCGTTGTCGGACGTTATCCTAACAACTAATACGGAACAGGCGTGTATCCGTCAAAGG

601 GGCTGAAAGGTCGCTTAAACCACGTCCAAAGATACAATAGCTAACGTATCGGGGAATGAA
                                                   R  I  P  S  H  V

661 CAATTCGATTATGGGTAGGCTCGCCCGCAAGTGATTGGCAAAGAAGTGGCATATAGAGAT
       I  R  N  H  T  P  E  G  A  L  S  Q  C  L  L  P  M  Y  L  Y

AflIII
                                                    ----DR3--->
  721 AAGCGCCTATATGGTTTAAAACGTCTGTAAGGCGATTTAAGCGGTGTCTGACGTGTTCTA
       A  G  I  H  N  L  V  D  T  L  R  N  L  R  H  R  V  H  E  L

781 ACCTTATGATAAGGTTTTCTATTGGGCAGACGATAGAAAAGCAAATAGAGCGATATACGT
       R  I  I  L  N  E  I  P  C  V  I  S  F  C  I  S  R  Y  V  H

841 GGTTGATACAAGCGATATGATTCTGAATTATACCTTGAACAATTTAAAAAGTCCTAAATA
       N  I  C  A  I  H  N  Q  I  I  G  Q  V  I <ORF2

901 CTTAGGGCTTCCTCTGCTCAAATCAAACTGATTGCCCTTGTTGATTGTGATTTACATTTG

961 GTGGTGTTATTATGAAAGCGTATATATTTCTATATCATGATATTTTAATTCTTTTTTAGA
                                                ORF1>  Y  F  N  S  F  L  E

----DR2----->
 1021 AAGGAGTCTATCTGTGACTATACTTTTTCAAGATGTTCCTGTTTCTGTTTGGGAAATCAA
       R  S  L  S  V  T  I  L  F  Q  D  V  P  V  S  V  W  E  I  N
```

FIG. 3A

```
1081 TAAGAATACCCCTCAGCCCGATTGGGTTAAAAACTGTTTTGAAAATAATACTATGGTTTG
        K  N  T  P  Q  P  D  W  V  K  N  C  F  E  N  N  T  M  V  W

1141 GTATGACAATAGGTTAAAAATACTTGTAAAAGCTATCAATCCTTCTCCAAAAAGAGATGT
        Y  D  N  R  L  K  I  L  V  K  A  I  N  P  S  P  K  R  D  V

1201 TAAATTAGGTTTACGAGATACCATGTTAGGTTATTATGGTGGTGGATTTGTAATGGGTAA
        K  L  G  L  R  D  T  M  L  G  Y  Y  G  G  G  F  V  M  G  N

AflIII
                                    ----DR3--->
1261 TATCGGTGATTATTTTGATGCAACAAATGGACGTGTTCTATCGAAAAAAAAGTTCTATAA
        I  G  D  Y  F  D  A  T  N  G  R  V  L  S  K  K  K  F  Y  K

SspI
1321 GCAATACGTTATAAACGAATAATATT
        Q  Y  V  I  N  E
```

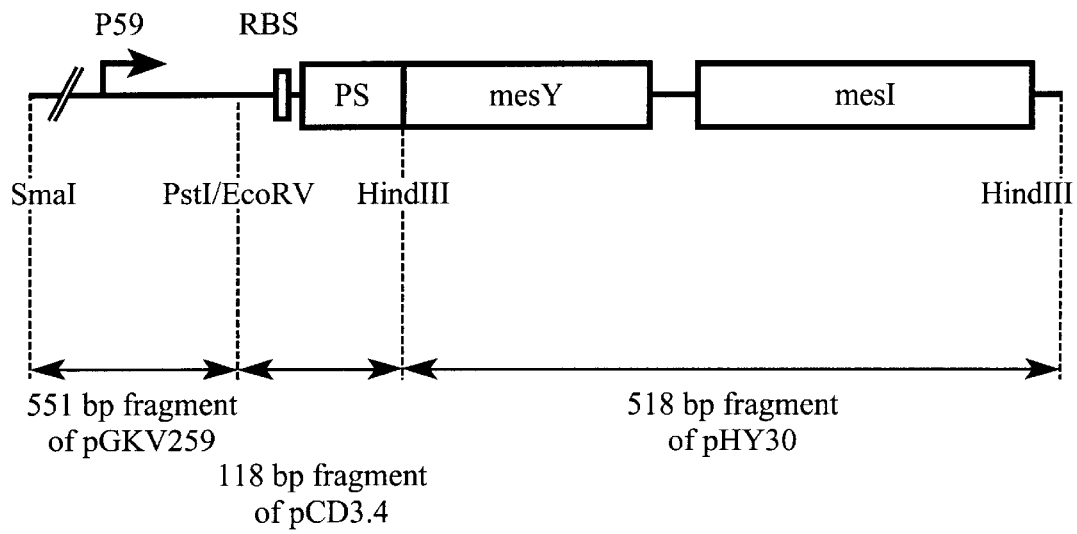

NON RCR LEUCONOSTOC PLASMID CAPABLE OF BEING TRANSFERRED INTO LACTIC ACID BACTERIA, USE AS CLONING AND EXPRESSING TOOL

FIELD OF THE INVENTION

The present invention relates to a plasmid which can be used, in particular, for transferring a heterologous gene into, and expressing it in, a bacterium, in particular a lactic acid bacterium.

BACKGROUND OF THE INVENTION

The plasmids of the lactic acid bacteria can be divided into two groups depending on their mode of replication, i.e. either a mode of replication in accordance with the rolling circle (RCR) model or a mode of replication which is similar to that of the chromosome (Theta). Genetic elements which are obligatory or otherwise, depending on the mode of replication of the plasmid, are present in the nucleic acid sequence of the plasmid. These genetic elements can be genes which are directly involved in the replication of the plasmid, specific nucleic acid sequences and nucleic acid sequences which form specific structures.

Up until now, many cloning and expression vectors which have been developed for the lactic acid bacteria have been based on RCR plasmids which have been isolated from lactic acid bacteria (Leenhouts et al., 1991). While their main advantage resides in their broad host spectrum, their unstable nature represents a barrier to using them.

Theta plasmids derived from lactic acid bacteria have been described (Hayes et al., 1990; Kiewiet et al., 1993, Frère et al., 1993). In particular, they display good stability and provide the possibility of transferring inserts of substantial size. Their main disadvantage is, however, that of a narrow host spectrum. For this reason, broad-host-spectrum vectors of the theta type used for cloning and expressing heterologous genes in lactic acid bacteria have been constructed from plasmids which have been isolated from enterococci (Simon and Chopin, 1988) or staphylococci (Le Chatelier et al., 1993). However, it is difficult to envisage using them for food-processing purposes in particular because they are not harmless.

SUMMARY OF THE INVENTION

The authors of the present invention have now isolated a plasmid which has been given the reference pTXL1, which is harboured by lactic acid bacterial strains, i.e. the strains *Leuconostoc mesenteroides* Y110 and *Leuconostoc mesenteroides* Y111, respectively, whose mode of replication has been established as not being that of the RCR type and which exhibits a high degree of stability and a broad host spectrum within lactic acid bacteria.

Plasmids which possess these properties are novel and are described for the first time within the context of the present invention.

The invention therefore relates to a plasmid whose mode of replication is not of the RCR type and which is capable of being transferred stably within lactic acid bacteria which belong to at least three different genera.

Advantageously, the plasmid is derived from lactic acid bacteria, in particular lactic acid bacteria of the genus Leuconostoc, in particular *Leuconostoc mesenteroides*.

Within the meaning of the present invention, the phrase plasmid which is capable of being transferred stably within *Leuconostoc mesenteroides* lactic acid bacteria is understood as signifying that the plasmid is maintained in the host cell into which it has been transferred, in the absence of selection pressure, after 75 generations, preferably after 90 generations, and more especially after 100 generations, with an apparent size which is equal to the size of the native plasmid apart from any inserts which it may possibly contain, including when it has been modified by the insertion of a sequence of a size as great as 4 kb, as long as the insertion is not effected into the parts of the plasmid which are required for its replication.

The plasmids according to the invention can advantageously be stably transferred into lactic acid bacteria which belong to the genera Leuconostoc; Lactobacillus, Pediococcus and Enterococcus, in particular the following species *Leuconostoc mesenteroides, Lactobacillus sake* and *Pediococcus acidilactici*.

The inventors, who are the authors of the present invention, have furthermore sequenced the plasmid pTXL1 and analysed its nucleic acid sequence.

They have located and determined a sequence fragment which is designated SEQ ID No. 1 below, which has a length of 1346 bp, and which contains all the elements which are required for the plasmid to replicate autonomously. This sequence has been designated "minimum replicon".

The invention therefore also relates to a plasmid as previously defined, which plasmid comprises the nucleotide sequence SEQ ID No. 1 or a sequence which differs from this sequence by the insertion, deletion or mutation of from one to several base pairs, and which retains the ability to replicate.

The total nucleic acid sequence of plasmid pTXL1 has been determined and is designated sequence SEQ ID No. 2.

The invention therefore also relates to a plasmid as previously defined, which plasmid comprises the nucleotide sequence SEQ ID No. 2 or a sequence which differs from this sequence by the insertion, deletion or mutation of one or several base pairs and which retains the ability of the plasmid to replicate stably in bacterial host cells which are of the lactic acid type and which belong to at least three different genera.

Two different strains of lactic acid bacteria harbouring the plasmid have been deposited in a microorganism collection.

The strain Y110 was thus deposited in the Collection Nationale de Culture de Microorganismes (CNCM) [National Collection of Microortanism Cultures] (Institut Pasteur, 28 rue du Docteur Roux, 75724, Paris cedex 15, France) on Oct. 30, 1997 under the number I-1936.

The strain Y111 was thus deposited in the Collection Nationale de Culture de Microorganismes (CNCM) on Oct. 30, 1997 under the number I-1937.

The plasmids, comprising, where appropriate, a heterologous sequence inserted into the plasmid DNA, are transferred into the host cells using known techniques.

Mention may, in particular, be made of the technique of electroporation, in particular that electroporation technique developed by transforming lactic acid bacteria, in particular Leuconostoc, Lactobacillus and Pediococcus.

The invention also relates to bacterial host cells which harbour a plasmid according to the invention, in particular the strains *Leuconostoc mesenteroides* Y110 and Y111 harbouring the plasmid pTXL1.

Because of the breadth of the host spectrum, the plasmids according to the invention constitute outstanding tools for cloning and expressing heterologous nucleotide sequences in host lactic acid bacteria.

In particular, the plasmids according to the invention can be used for expressing heterologous proteins, such as nisin and mesentericin Y105, which are bacteriocins, proteins for resistance to these bacteriocins, also termed immunity proteins, and/or a protein for resistance to an antibiotic, for example erythromycin, in host cells, in particular lactic acid bacteria.

The expression of heterologous proteins of the above-mentioned type is particularly attractive inasmuch as it makes it possible, when the heterologous protein is a bacteriocin, for a lactic acid bacterium, which is present in a medium for a given function and which is totally harmless, to be caused to secrete a substance which is capable of preventing the growth of other bacteria which are undesirable if not to say pathogenic, in particular Listeria bacteria, which have a tendency to grow in lactic acid media.

When the heterologous protein is the protein for immunity to a bacteriocin, the expression of this protein has the value of conferring on the host lactic acid bacterium resistance to the bacteriocin while at the same time preventing the growth of unwanted harmful or pathogenic bacteria.

Similarly, when the heterologous protein is a protein for resistance to an antibiotic, it is then possible to add the antibiotic in question to the medium in which the host bacterium is present without harming the growth and metabolism of this host bacterium while at the same time acting on the growth of unwanted microorganisms.

The invention therefore also relates to the use of a plasmid as described above as a tool for cloning and expressing heterologous nucleic acid sequences in host cells, in particular lactic acid bacteria, in particular the lactic acid bacteria which are mentioned above.

The invention thus also relates to a modified plasmid which is obtained from a plasmid as previously described by inserting a heterologous nucleic acid sequence, preferably a nucleic acid sequence which encodes a heterologous protein or peptide.

The nucleic acid sequence of interest can be inserted, using the appropriate molecular biological tools, in particular restriction enzymes, ligase, etc., into any site in the nucleic acid sequence of the plasmid, in particular in the sequence SEQ ID No. 2 apart from the sequence SEQ ID No. 1.

The length of the nucleic acid sequence encoding the heterologous protein or peptide can be up to at least 4 kb, if not larger.

The invention also relates to host cells which harbour a modified plasmid according to the invention, in particular a plasmid which comprises the sequence SEQ ID No. 1 and all or part of the sequence SEQ ID No. 2 into which a heterologous nucleotide sequence is inserted.

These host cells are, in particular, lactic acid bacteria, more especially belonging to the genera Leuconostoc, Lactobacillus and Pediococcus, preferably to the species *Leuconostoc mesenteroides, Lactobacillus sake* and *Pediococcus acidilactici*.

BRIEF DESCRIPTION OF THE DRAWINGS

The cloning of plasmid pTXL1, and the analysis of its sequence, will be described below, as will a recombinant plasmid which is constructed from pTXL1, while referring to FIGS. 1 to 4 in which:

FIG. 3 depicts the nucleic acid sequence of the SalI/SspI fragment (SEQ ID NO:1) which constitutes the "minimum replicon" of pRXL1. The restriction sites which were used for the constructs depicted in FIG. 2 are indicated. The restriction sites which were used for the constructs depicted in FIG. 2 are indicated. The part which is deleted in plasmid pFBY065 is contained between the SalI site and the vertical arrow (position 314). The inverted repeat sequences (IR, unbroken arrows) and repeat sequences (DR, dashed arrows) are indicated above the sequence. The translation of the open reading frames ORF1 (SEQ ID NO:4) and ORF2 (SEQ ID NO:3) is shown below the sequence.

FIG. 4 illustrates the genetic organization of the DNA fragment which is cloned into pFBYC051E, which fragment permits secretion of the mesentericin Y105. This DNA fragment is derived from the plasmid pFBYC07, which is described by Diet et al. (1997). It includes, from left to right:

Figure 1:
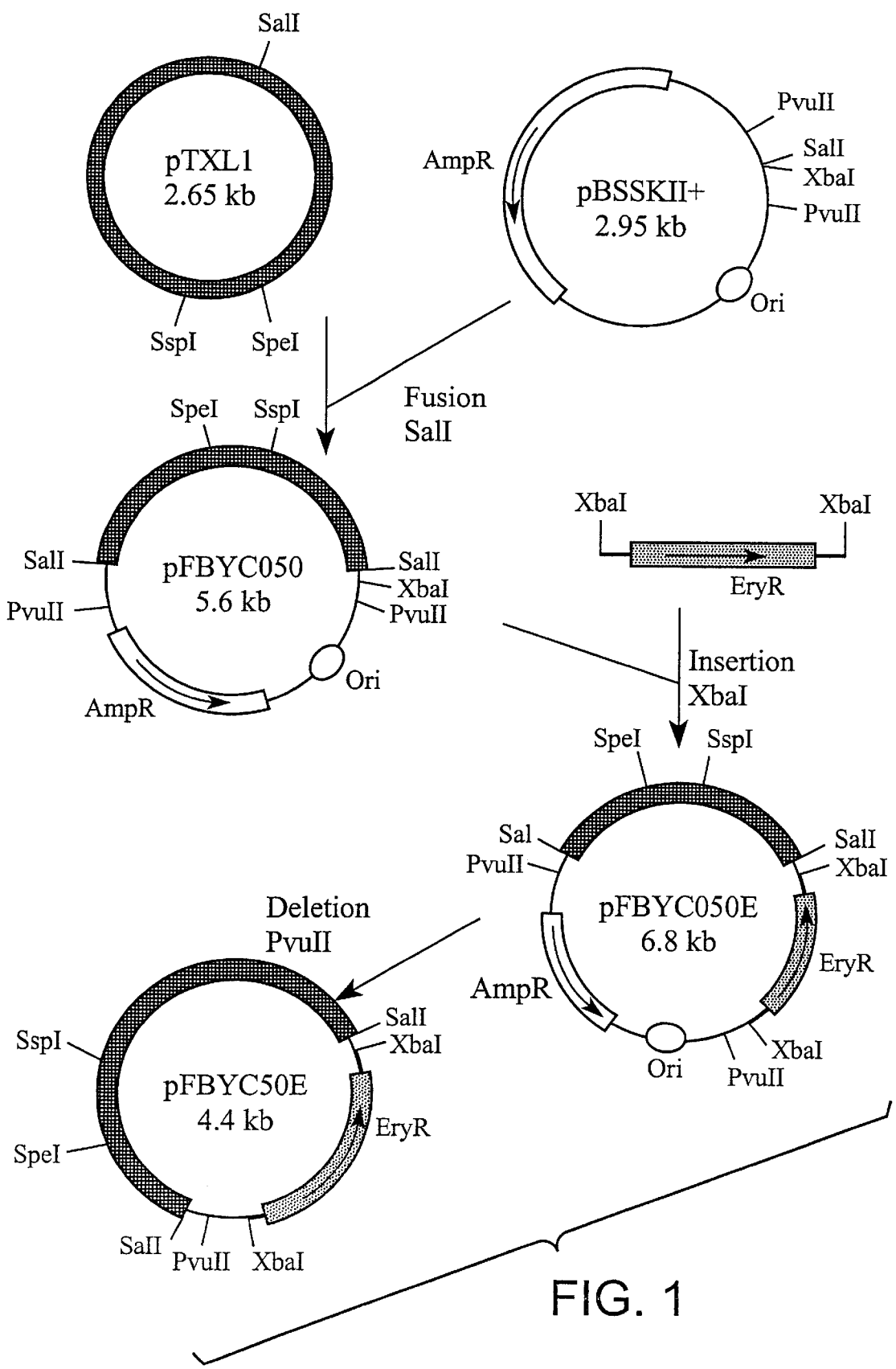
FIG. 1 illustrates the construction of the plasmid pFBYC50E. In a first step, pTXL1 was linearized with the enzyme SalI in order to fuse it with the plasmid PBSSKII+, which was also linearized at the SalI site. In a second step, the gene for resistance to erythromycin EryR, which was isolated from the plasmid pGhost91SS1, was inserted into the XbaI site in order to give the construct pFBYC050E. In a final step, a PvuII deletion carried out on the pFBYC050E construct eliminates approximately 85% of the DNA of pBSSKII+ origin thereby giving rise to the cloning vector pFBYC50E.

a 551 bp SmaI/PstI fragment derived from pGKV259 (Van Der Vossen et al. (1987)).

a 118 bp EcoRV/HindIII fragment derived from pCD3.4 (Worobo et al. (1995)).

a HindIII fragment obtained by carrying out a PCR on the plasmid pHY30 (Fremaux et al. (1995)).

P59: the p59 promoter from *L. lactis* (Van Der Vossen et al., 1987)); RBS: ribosome binding site; Ps: gene fragment encoding the signal peptide of divergicin A (Worobo et al. (1995)); mesY: part of the gene encoding the mature form of mesentericin Y105, mesI: gene encoding the protein for immunity to mesentericin.

DETAILED DESCRIPTION OF THE INVENTION

The strains employed in these studies are listed in Table I. They were propagated by conventional microbiological methods in culture media and at temperatures which were recommended for each species. When necessary, erythromycin or ampicillin were added to the culture media at the rate of 5 $\mu$g of erythromycin/ml, in the case of the cultures of lactic acid bacteria, and of 150 $\mu$g of erythromycin/ml and 75 $\mu$g of ampicillin/ml in the case of the *Escherichia Coli* cultures.

The plasmids which were characterized, used and constructed are described in Table II.

The general molecular biological techniques employed have been described by Sambrook et al. (1989). The restriction and modification enzymes were used in accordance with the recommendations of the supplier (GIBCO-BRL). The electroporation protocols which were implemented for transforming Lactobacillus and Pediococcus are described by Berthier et al. (1996) and Raya et al. (1992), respectively. The technique of Raya et al. (1992) was used for transforming Leuconostoc; in this case, the bacteria are firstly cultured in the presence of 0.6 g of DL-threonine/l. For preparing the plasmid pTXL1, a plasmid extract was obtained from the *Leuconostoc mesenteroides* strain Y110 using the method described by Muriana and Klaenhammer (1991) and then purified from an agarose gel of the ®SeaPlaque GTG (FCM BioProducts) type using the ®Prep-a-Gene (Bio-Rad) kit. The computer analysis of the nucleic acid and protein sequences which were determined was carried out using the ®GCG (USA) software.

Activity antagonistic to *L. ivanovii* was detected using the "drop test" method. A soft BHI medium (Difco) agar (0.6% agar), which has been seeded to the extent of 0.2% with a culture of *L. ivanovii* CLIP257 which is in the exponential phase of growth, is used to cover a BHI medium which contains 1.5% agar. Five µl of a supernatant from a culture are then adsorbed onto the surface of the "soft" agar after the latter has solidified. The results are read after 18 hours of incubation at 30° C. In order to test the protein nature of the antagonists which are detected, 5 µl of a 10 mg/ml solution of ®Proteinase K (Sigma) are adsorbed at about 2 cm from the site at which the culture supernatant was deposited. The presence of an antagonist is manifested by the appearance of a halo (circular shape) of growth inhibition. This inhibition halo will be partially destroyed (crescent shape) in the presence of proteinase K if the antagonist is protein in nature. The active molecule produced by the clone DSM20484 (pFBYC070) was purified using the method described by Biet et al., (1997). Its molecular mass was then determined by mass spectrometric analysis (Perkin Elmer SCIEX API 165).

1. Detection of Plasmid pTXL1

The strain Y110 was isolated in the laboratory (IBMIG, Poitier University) from unpasteurized goat milk samples and selected on account of its antagonistic property with regard to Listeria ssp. Its taxonomy was determined by the "Deutsche Sammlung von Mikroorganismen" (DSM, Germany); strain Y110 is strain of *Leuconostoc mesenteroides* subspecies *mesenteroides*. Its biochemical characteristics are given in Table III.

The presence of extra chromosomal (or plasmid) DNA in strain Y110 was determined. This strain harbours five plasmids which are characteristic for the strain. The plasmid which has a size of approximately 2.6 kbp and which is designated pTXL1 is the subject of the remainder of the study.

2. Cloning Plasmid pTXL1

The procedure is illustrated in FIG. 1.

The available molecular biological tools are not suitable for carrying out a direct analysis in *Ln. mesenteroides*. Molecular analysis of plasmid pTXL1 therefore requires it to be initially cloned into *E. coli*, which is a species which is routinely employed for this type of analysis. The cloning involves separating plasmid pTXL1 from the other plasmids harboured by strain Y110 and fusing plasmid pTXL1 to the cloning vector pBluescript II SK+(pBSSKII+, Stratagene).

The plasmids belonging to strain Y110 were separated by electrophoresis on an 0.8% ®SeaPlaque GTG agarose gel. The portion of the gel containing plasmid pTXL1 was isolated and the plasmid was purified.

Fusing plasmid pTXL1 and the cloning vector pBSSKII+ requires a preliminary study in order to define the unique restriction sites which are common to these two plasmids. The restriction sites contained in PBSSKII+ are described in the literature (Stratagene). In order to search for the unique restriction sites in pTXL1, a portion of plasmid pTXL1, obtained as described above, is acted on by a variety of restriction enzymes. It was possible to define unique restriction sites for the restriction enzymes SalI, SpeI and SspI in pTXL1 (FIG. 1). Plasmid pTXL1 and the cloning vector PBSSKII+ were linearized with the restriction enzyme SalI and then purified using the ®Prep-A-Gene DNA purification kit. The two plasmids which had thus been linearized were then ligated using T4 DNA polymerase and subsequently introduced into the strain *E. coli* DH5α. The resulting fusion plasmid pTXL1/pBSSKII+ was designated pFBYC050 and has a size of 5.6 kb.

3. Molecular Characterization of Plasmid pTXL1

Determination of the Nucleic Acid Sequence

The complete nucleic acid sequence of plasmid pTXL1 was determined by the method of Sanger et al. (1977) using the pFBYC050 construct and employing the ®AutoRead (Pharmacia) sequencing kit and an automated DNA sequencer (ALF, Pharmacia).

The sequence was designated sequence SEQ ID No. 2.

The construct pFBYC051 was prepared by the method described for pFBYC050 but using the restriction enzyme SpeI. This construct was prepared in order to verify the sequence of plasmid pTXL1 at the SalI restriction site (in particular in order to ensure that the complete plasmid had been cloned). In addition, the complete nucleic acid sequence of plasmid pTXL1 was determined once again using the pFBYC051 construct, thereby enabling the initially obtained sequence to be confirmed.

Analysis of the Nucleic Acid Sequence of pTXL1

The nucleic acid sequence of pTXL1 was compared with the nucleic acid sequences which are listed in the GenBank (USA) and EMBL (Germany) databases. A region of pTXL1 of approximately 200 bp in size displays strong sequence identity with the pWV01-type RCR plasmid family (Leenhouts et al., 1991). The remainder of the sequence does not display any identity with the sequences contained in the databases.

This homology with the pWV01-type plasmids would suggest a replication in accordance with the rolling circle model (Gruss and Ehrlich, 1989). However, components which are essential to this mode of replication are absent from pTXL1, in particular the gene which encodes the replicase, which is a component which is obligatory for RCR replication. Furthermore, it has never been possible to detect a single-stranded form of plasmid pTXL1, whereas this intermediate type is generally detected in cells which harbour an RCR plasmid. Finally, the inventors subsequently demonstrated that the sequence displaying homologies with RCR plasmids was not required for replicating the plasmid (see FIG. 2, plasmid FBY).

The fine analysis of the sequence, in particular the search for open reading frames and inverted sequences and direct repeats, was carried out on the minimum replicon, as described below.

4. Construction of a Cloning Vector Using pTXL1

Introduction of a Selection Marker into Plasmid pFBYC050

The lactic acid bacteria are genetically transformed using the electroporation method (Bio-Rad). The efficiency of this transformation is very dependent on the strains employed. In *L. lactis*, it usually varies from 10 to $10^6$ transformants per µg of DNA depending on the receptor strain. After optimizing the transformation technique described by Raya et al. (1992), the inventors were able to select a strain (*Ln. mesenteroides* DSM20484) which displayed an elevated degree of transformability (approximately $10^5$ transformants per µg of DNA).

Nevertheless, the transformation rate of the strains is still very low. For example, the transformation rate for DSM20484 is less than 1 bacterium transformed per $10^5$ bacteria treated. It is therefore absolutely necessary to introduce a marker for selecting the bacteria which are transformed during the electroporation. Genes for resistance to antibiotics are normally used as positive selection markers. The gene for resistance to erythromycin, derived from plasmid pAMβ1, is known to function in lactic acid bacteria, in particular in leuconostoc bacteria. Consequently, the gene encoding resistance to erythromycin (eryR), as obtained from the cloning vector pGhost91SS1 (Maguin et al., 1996), was introduced into the unique XbaI restriction site in pFBYC050 as shown in FIG. 1. This construct, termed pFBYC050E, was initially obtained in *E. coli* and then transferred successfully into DSM20484.

Elimination of the pBSSKII+ Replicon Plasmid pFBYC050E is therefore operational in the DSM20484 strain. However, in order to be able to confirm that the functions supplied by plasmid pTXL1 are responsible for the replication of this plasmid, the replication functions carried by pBSSKII+ have to be eliminated.

This deletion was effected by cleaving twice with the restriction enzyme PvuII, as shown in FIG. 1. This double cleavage excises a fragment which constitutes more than 85% of the pBSSKII+, including all its replication functions. The plasmid resulting from this manipulation, termed PFBYC50E, was successfully introduced into the DSM20484 strain, thereby unequivocally demonstrating the ability of the replicon to function in this configuration, which can be likened to a cloning vector.

Locating the Minimum Replicon

In order to delimit more closely the elements encoded by pTXL1 and required for its replication, various fragments of the plasmid were fused with the vector PBSSKII+. A marker gene (gene for resistance to erythromycin) was then introduced into these constructs. These plasmids were obtained in *E. coli* as a consequence of the replication functions supplied by pBSSKII+ and are shown in Table II and in FIG. 2. The replication functions supplied by pBSSKII+ were therefore not eliminated since the inventors have demonstrated above that these functions do not play any role in this configuration.

Figure 2:
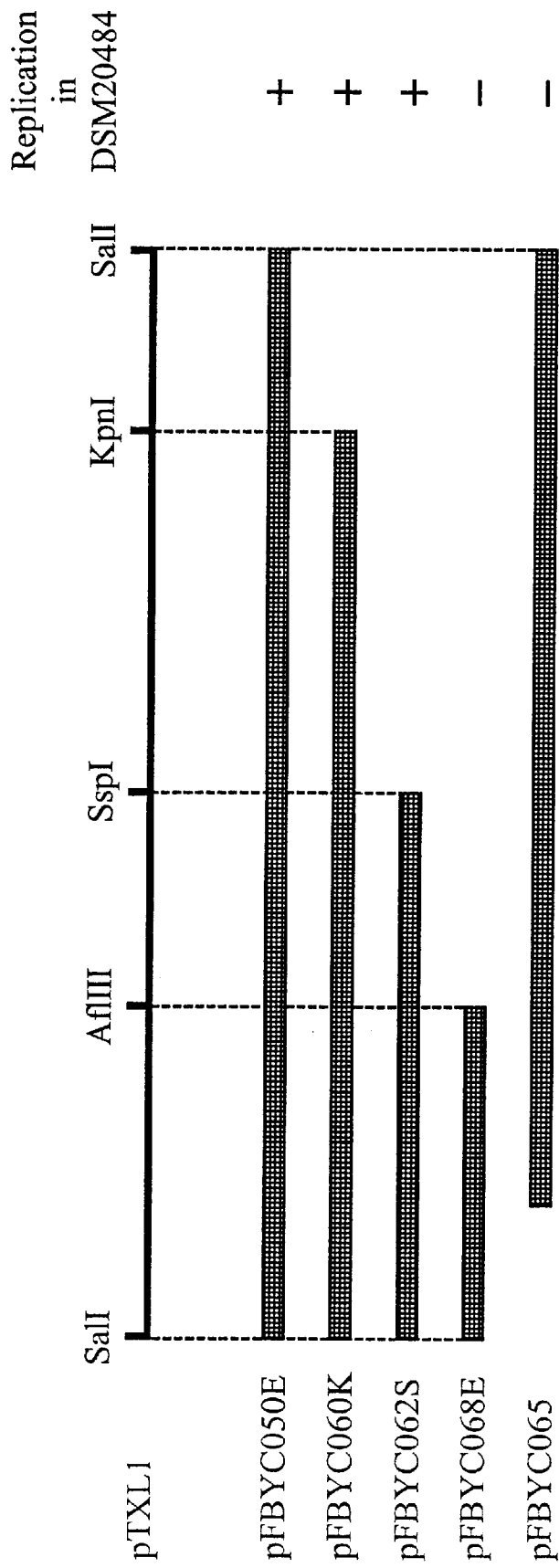
FIG. 2 depicts the partial restriction map of pTXL1. The stars indicate a region of strong sequence homology with RCR plasmids. The grey-tinted bars indicate the pTXL1 fragments which were introduced into the pBSSKII+ vector at the same time as the gene for resistance to erythromycin. The names of the plasmids which are obtained in this way are given on the left of the figure. The ability (+) or inability (−) of the plasmids to replicate in the *Leuconostoc mesenteroides* strain DSM20484 is shown on the right of the figure.

Subsequently, these constructs were used for transforming DSM20484. Given the high transformation efficiency obtained for this strain (from 104 to 105 transformants per µg of DNA), the view was taken that the totality of the replication functions was not present in the cloned pTXL1 fragment when no transformant was obtained. The results which were obtained, and which are shown in FIG. 2, made it possible to define a minimum fragment of 1346 bp in size which was delimited by the SalI and SspI restriction sites and which contained all the elements which were required for pTXL1 to replicate autonomously. This fragment, which was termed the minimum replicon, comprises the sequence SEQ ID No. 1.

5. Analysis of the pTXL1 Minimum Replicon
Searching for Open Reading Frames (ORF)

The literature is full of examples of plasmids which have been isolated from lactic acid bacteria, and which encode proteins, termed replicases, which play an essential role in the replication of these plasmids. ORFs were therefore sought in the pTXL1 minimum replicon. Two short ORFs were found (FIG. 3): ORF1 (nucleotides 1000 to 1341) and ORF2 (nucleotides 883 to 640). Sequences resembling ribosome binding sites (RBSs), which are required for translating ORFs into proteins, were detected in their immediate vicinity. However, no translation initiation codon is located at an appropriate distance from these potential RBSs, suggesting that these ORFs might not be translated. The protein sequences were nevertheless deduced from these ORFs and compared with the protein sequences contained in the GenBank (USA) and SwissProt (EMBL, Germany) databases. They are in no way similar to proteins which have already been described.

ORF1 and ORF2 are affected by the cleavage with AflIII which is carried out in order to obtain pFBYC068E (FIG. 2). This construct is unable to replicate autonomously, and it is therefore possible that these sequences play a role in the replication of pTXL1.

Searching for Repeat Sequences (DR) and Inverted Repeat Sequences (IR)

It is known from the literature that DR and/or IR sequences are involved in the replication of a large number of plasmids. They possess the distinctive characteristic of being able to induce the formation of secondary structures. While some of them have been described, they are not present in pTXL1. On the other hand, two IR sequences (referenced IR1 and IR2, FIG. 3) were detected within the pTXL1 minimum replicon. They are capable of generating secondary structures whose calculated $\Delta G_0$ values are $-10.6$ and $-22.4$ kcal/mol. The presence of 3 DR sequences, referenced DR1, DR2 and DR3 in FIG. 3, is also to be noted The region containing the IR1 and DR1 elements is absent in plasmid pFBYC065, which does not replicate in DSM20484. It is therefore possible that these sequences have a role in pTXL1 replication.

6. Performance of Plasmid pFBYC50E
Stability

The majority of cloning vectors of alimentary quality which have been developed for the lactic acid bacteria are derived from plasmids of the RCR type and prove to be unstable in the absence of selection pressure. In order to assess the stability of plasmid pFBYC50E, a clone of DSM20484 harbouring pFBYC50E was isolated on selective MRS culture medium (containing 10 µg of erythromycin/ml). This clone was then used to inoculate non-selective MRS media (not containing any erythromycin) successively, at 1:1000 dilution, so as to multiply the clone over at least 100 generations. The stability of the plasmid is then assessed by the proportion of subclones which have retained the plasmid. This measurement is performed by comparing a dilution of the final culture (after 100 generations) which is spread on selective medium and on non-selective medium. The stability of the plasmid is expressed as a percentage and corresponds to:

$$\frac{\text{Number of subclones obtained on selective medium}}{\text{Number of subclones obtained on non-selective medium}} \times 100$$

The results presented in Table IV clearly demonstrate the stability of plasmid pFBYC50E as compared with that of the RCR plasmid pFR18.

Host Spectrum

The host spectrum of the vectors which have been developed from plasmids which are of the Theta type and which have been isolated from lactic acid bacteria is generally narrow. Attempts were made to transform bacteria belonging to the main lactic acid groups, which are also those most frequently employed industrially, i.e. Lactobacillus, Pediococcus and Leuconostoc, with plasmid pFBYC50E. The strains selected were chosen in accordance with their level of transformability (*Lactobacillus sake* 23K; *Pediococcus acidilactici* PAC1.0 and *Leuconostoc mesenteroides* DSM20484) when using the most suitable transformation protocols. As Table V shows, it was possible to obtain transformants with all the strains.

Transformation Efficiency

Plasmid pFBYC50E and plasmid pFBYC018E, which is a vector which was constructed from a plasmid of the RCR type derived from *Ln mesenteroides*, were used to assess the efficiency of the transformation of the strain *Lb. sake* 23K by electroporation. These two plasmids possess the same selection marker and were prepared from the same host strain. Equivalent quantities of plasmids and the same preparation of electrocompetent bacteria were employed. Based on three independent experiments, the transformation yields obtained with plasmid pFBYC50E are approximately $10^4$ transformants per µg of DNA, that is an efficiency which is approximately 1000 times greater than that obtained with the vector which was constructed from pFR18.

7. Use of the Replicon for Producing a Bacteriocin in Lactic Acid Bacteria

The bacteriocins are antibacterial peptides. In particular, mesentericin Y105 is a bacteriocin which is produced by *Ln mesenteroides* Y105 and which displays activity against *Listeria*. Its genetic determinants have been described (Fremaux et al., 1995), with this study demonstrating that its production in the extracellular medium depends on a specific transport system. In order to avoid the potential problems linked to this transport system when heterologously expressing the bacteriocin, a gene assembly was constructed which is capable of secreting mesentericin Y105 (Biet et al., 1997). This is because secretion is a universal transport system in bacteria. This gene assembly was then introduced into a plasmid derived from pTXL1.

Secretion of Mesentericin Y105

In order to enable mesentericin Y105 to be secreted, several genetic elements, which function in lactic acid bacteria, were combined as described in FIG. 4 and by Biet et al. (1997). These elements are:

1. the constitutive promoter p59, derived from *L. lactis* (Van der Vossen et al., 1987);
2. the ribosome binding site (RBS) which is located upstream of the structural gene for divergicin A (dvnA), which is produced by *Carnobacterium divergens* LV13 (Worobo et al., 1995);
3. the part of the structural gene for divergicin A (dvnA) which encodes the signal peptide (Worobo et al., 1995);
4. the part of the structural gene for mesentericin Y105 (mesY) which encodes the mature part of mesentericin Y105 (Fremaux et al., 1995);
5. the mesI gene, which encodes the protein for immunity to mesentericin Y105.

Construction of the Plasmid Which Enables Mesentericin Y105 to be Secreted

Construction of pFBYC051E: The construction was performed by introducing a BamHI fragment, encoding resistance to erythromycin, into plasmid pFBYC051, as described for pFBYC050E in FIG. 1.

Construction of pFBYC070: The DNA fragment enabling mesentericin Y105 to be secreted (described in FIG. 4) was introduced between the SmaI and HindIII restriction sites in plasmid pFBYC051E. This construction was performed directly in the *Ln. mesenteroides* DSM20484 strain, given the toxicity of mesentericin Y105 when cloned in *E. coli*.

Expression of Mesentericin Y105 by the DSM20484 Clone Harbouring Plasmid pFBYC070

It was possible to use the drop test method to visualize the presence of an active antagonist of *L. ivanovii* CLIP257 in culture supernatants derived from the DSM20484 strain harbouring pFBYC070. The protein nature of the active molecule was demonstrated by its sensitivity to proteinase K. The antagonist was then purified to 99% purity using the method developed and described by Biet et al., (1997) and its molecular mass was determined by spectrometry. The value obtained, i.e. 3868±0.1 Da, corresponds exactly to the theoretical mass calculated from the reduced form of mesentericin Y105.

TABLE I

Specifications of the bacterial strains employed.

| Strains | Specification | References |
|---|---|---|
| *Escherichia coli* DH5α | recA EndAI gyrA96 thi-1 hsdR17 supE44 Δlac u169(φ80 dlacZΔM15)deoRF⁻λ⁻ | GIBCO-BRL |
| *Leuconostoc mesenteroides* ssp. Mesenteroides | | |
| Y110 | wild-type strain | present invention |
| Y111 | wild-type strain | present invention |
| Y105 | wild-type strain | Fremaux et al. (1995) |
| FR52 | wild-type strain | Mathieu et al. (1993) |
| *Leuconostoc mesenteroides* ssp. Dextranicum | | |
| DSM 20484 | wild-type strain | DSM |
| *Lactobacillus sake* 23K | plasmidless strain | Berthier et al. (1996) |
| *Pediococcus acidilactici* PAC1.0 | wild-type strain | Marugg et al. (1992) |
| *Listeria ivanovii* CLIP257 | wild-type strain | Pasteur Institute Collection |

TABLE II

Specification of the plasmids employed or constructed.

| Plasmids | Specification | References |
|---|---|---|
| pTXL1 | natural *Ln mesenteroides* Y110 plasmid | unpublished |
| pBSSKII+ | pBluescript II SK+, *E. coli* cloning vector | Stratagene |
| pGKV259 | *E. coli*/lactic acid bacteria shuttle cloning vector | Van der Vossen et al. (1987) |
| pHY30 | natural *Ln Mesenteroides* Y105 plasmid | Fremaux et al. (1996) |
| pCD3.4 | natural Carnobacterium divergences LV13 plasmid | Worobo et al (1995) |
| pGhost91SS1 | cloning vector which is the source of eryR | Maguin et al. (1996) |
| pFR18 | natural *Leuconostoc mesenteroides* ssp. Mesenteroides FR52 plasmid | Biet et al. (1997) |
| pFBYC018E | Derivative of pFR18 | Biet et al. (1997) |
| pFBYC050 | insertion of SalI– linearized pTXL1 into the SalI site of pBSSKII+ | present invention |
| pFBYC051 | insertion of SpeI– linearized pTXL1 into the SpeI site of pBSSKII+ | present invention |
| pFBYC052 | insertion of SspI– linearized pTXL1 into the SmaI site of pBSSKII+ | present invention |
| pFBYC050E | pFBYC050::ErmR | present invention |
| pFBYC50E | pFBYC050E from which pBSSKII has been deleted by double | present invention |

TABLE II-continued

Specification of the plasmids employed or constructed.

| Plasmids | Specification | References |
|---|---|---|
| pFBYC065 | pFBYC050E from which 312 bp have been deleted restriction with PvuII | present invention |
| pFBYC060K | pFBYC050E from which 482 bp have been deleted by restriction with KpnI and KpnI [sic] | present invention |
| pFBYC062S | pFBYC052E from which 1400 bp have been deleted by restriction with SalI and SspI | present invention |
| pFBYC068E | pFBYC050E from which 1893 bp have been deleted by restriction with SalI and AF1III | present invention |
| pFBYC051E | pFBYC051::ErmR | present invention |
| pFBYC07 | secretion vector derived from pGKV259 and pCD3.4 | Biet et al. (1997) |
| pFBYC069 | insertion of the p59/dvnA signal fusion into pFBYC051E | present invention |
| pFBYC070 | insertion of the mature mesY and mesI genes into pFBYC069 | present invention |

TABLE III

Description of the strain *Leuconostoc mesenteroides* subsp. *mesenteroides* Y110 given by the "Deutsche Sammlung von Mikroorganismen" (DSM).
Gram-positive coccus which appears in pairs or in short chains and which is facultatively anaerobic; products of glucose fermentation: lactic acid, ethanol and $CO_2$.

| Mobility | − | Growth at 45° C. | − |
|---|---|---|---|
| Spore formation | − | Gas from glucose | + |
| Catalase | − | Gas from gluconate | − |
| Growth at 15° C. | + | | |
| Production of acid from: | | | |
| Ribose | + | Glucose | + |
| Arabinose | − | Lactose | − |
| Xylose | + | Maltose | + |
| Rhamnose | − | Sucrose | + |
| Manitol | − | Trehalose | + |
| Sorbitol | − | Cellobiose | − |
| Ribitol | − | Raffinose | − |
| Glycerol | − | Melibiose | − |
| Fructose | + | Melezitose | − |
| Mannose | + | Salicin | − |
| Galactose | + | Gluconate | − |

$NH_3$ from arginine-

Configuration of the lactic acid: D(−)

No meso-diaminopimelic acid in the cell hydrolysate.

Type of peptidoglycan: A3α, Lys-Ser-Ala$_2$

TABLE IV

Stability of plasmid pTXL1 derivatives in the absence of selection pressure.

| Plasmids | Stability* |
|---|---|
| pFBYC050E | 100 |
| pFBYC50E | 100 |
| Control RCR plasmid (pFR18) | 3 |

TABLE IV-continued

Stability of plasmid pTXL1 derivatives in the absence of selection pressure.

| Plasmids | Stability* |
|---|---|

*percentage of clones which were isolated after 100 generations and which harboured the plasmid

TABLE V

Host spectrum of the pTXL1 derivatives (pFBYC050E and/or pFBYC50E) were used [sic].

| Strains | Transformability |
|---|---|
| *Leuconostoc mesenteroides* LM20484 | + |
| *Lactobacillus sake* 23K | + |
| *Pediococcus acidilactici* PAC1.0 | + |

REFERENCES

Berthier, F., M. Zagorec, M. Champomier-Vergès, S. D. Ehrlich, and F. Morel-Deville. 1996. Efficient transformation of *Lactobacillus sake* by electroporation. Microbiology. 142: 1273–1279.

Biet, F., J. M. Berjeaud, R. W. Worobo, Y. Cenatiempo, and C. Fremaux. 1997. Heterologous expression of mesentericin Y105 using the general secretion pathway (GST) or the dedicated transport system (DTS) in gram-positive and gram-negative bacteria. Soon to be submitted for publication in Microbiology.

Biet F., Cenatiempo, and C. Fremaux 1997, Nucleotide sequence analysis and characterization of pFR18 a small cryptic plasmid for *Leuconostoc mesneteroides* ssp. *Mesenteroides* Fr52 and its use as a vector. Submitted for publication.

Fremaux, C., Y. Héchard, and Y. Cenatiempo. 1995. Mesentericin Y105 gene clusters in *Leuconostos mesenteroides* Y105. Microbiology. 141: 1637–1645.

Frère, J., M. Novel, and G. Novel. 1993. Molecular analysis of the *Lactococcus lactis* subspecies *lactis* CNRZ270 bidirectional theta replicating lactose plasmid pUCL22. Molecular Microbiology. 10(5): 1113–1124.

Gruss, A., and D. Ehrlich. 1989. The family of interrelated single-stranded deoxyribonucleic acid plasmids. MICROBIOLOGICAL REVIEWS. June: 231–241.

Hayes, F., C. Daly and G. F. Fitzgerald. 1990, Identification of the minimum replicon of *Lactococcus lactis* subsp. *lactis* UC317 plasmid pCI305. Applied and Environmental Microbiology 56(1): 202–209.

Kiewiet, R., S. Bron, K. De Jonge, G. Venema, and J. F. M. L. Seegers. 1993. Theta replication of the lactococcal plasmid pWV02. Molecular Microbiology. 10(2): 319–327.

Le Chatelier, E., D. S. Ehrlich, and L. Jannière. 1993. Biochemical and genetic analysis of the unidirectional theta replication of the *S. agalactiae* plasmid pIP501. PLASMID. 29: 50–56

Leenhouts, K. J., B. Tolner, S. Bron, J. Kok, G. Venema, and J. F. M. L. Seegers. 1991. Nucleotide sequence and characterization of the Broad-host-range Lactococcal plasmid pWV01. PLASMID 26: 55–66.

Maguin, E., H. Prévost, D. S. Ehrlich, and A. Gruss. 1996. Efficient insertioal [sic] mutagenesis in Lactococci and other Gram-positive bacteria. Journal of bacteriology. 178 (3): 931–935.

Marugg, J. D., C. F. Gonzales, B. S. Kunka, A. M. Ledeboer, M. J. Pucci, M. Y. Toonen, S. A. Walker, L. C.

Zoetmulder, and P. A. Vandenbergh. 1992. Cloning, expression, and nucleotide sequence of genes involved in production of PA-1, a bacteriocin from *Pediococcus acidilactici* PAC1.0. APPLIED AND ENVIRONMENTAL MICROBIOLOGY. 58(8): 2360–2367.

Muriana, P. M., and T. R. Klaenhammer. 1991. Cloning, phenotypic expression and DNA sequence of the gene for lactacin F, an antimicrobial peptide produced by Lactobacillus spp. Journal of Bacteriology, 173(5): 1779–1788.

Raya, R. R., C. Fremaux, G. L. De Antoni, and T. R. Klaenhammer. 1992. Site-specific integration of the temperate bacteriophage fadh into the *Lactobacillus gasseri* chromosome and molecular characterization of the phage (attP) and bacterial (attB) attachment site. Journal of Bacteriology. 174: 5584–5592.

Sambrook, J., E. Fritsche, and T. Maniatis (ed.). 1989. Molecular cloning: a laboratory manual, NY: Cold Spring Harbor Laboratory.

Sanger, F., S. Nicklen, and A. R. Coulson. 1977. DNA sequencing with chain-terminating inhibitions. Proc. Natl. Acad. Sci. 74: 5463–5467.

Simon, D., and A. Chopin. 1988. Construction of a vector plasmid family and its use for molecular cloning in *Streptococcus lactis*. Biochimie. 70: 559–566.

Van Der Vossen, J. M. B. M., D. Van Der Lelie, and G. Venema. 1987. Isolation and characterization of *Streptococcus cremoris* Wg2-specific promoters. Applied and Environmental Microbiology. 53 (10): 2452–2457.

Worobo, R. W., M. J. Van Belkum, M. Sailer, K. L. Roy, J. C. Vederas, and M. E. Stiles. 1995. A signal peptide secretion-dependent bacteriocin from *Carnobacterium divergens*. Journal of Bacteriology. 177(11): 3143–3149.

---

What is claimed is:

1. An isolated plasmid which has a mode of replication not of the RCR type and which is capable of being transferred stably in host lactic acid bacteria which belong to at least three different genera, said plasmid comprising the nucleotide sequence of SEQ ID NO:1.

2. The isolated plasmid according to claim 1, wherein said plasmid is obtained from a lactic acid bacterium of the genus Leuconostoc.

3. The isolated plasmid according to claim 1, wherein said plasmid is obtained from a *Leuconostoc mesenteroides* lactic acid bacterium.

4. The isolated plasmid according to claim 1, wherein the host bacteria belong to at least the genera Leuconostoc, Lactobacillus and Pediococcus.

5. The isolated plasmid according to claim 1, wherein the host lactic acid bacteria belong to the species *Leuconostoc mesenteroides, Lactobacillus sake* and *Pediococcus acidilactici*.

6. The isolated plasmid according to claim 1, wherein said plasmid is stable in host Lactic acid cells after 75 generations, in the absence of selection pressure.

7. The isolated plasmid according to claim 1, which is stable in host cells after approximately 90 generations.

8. The isolated plasmid according to claim 1, which is stable in host cells after approximately 100 generations.

9. A host cell transformed with a plasmid according to claim 1, wherein the untransformed host cell does not naturally comprise said plasmid.

10. A modified plasmid obtained by inserting a heterologous nucleotide sequence into a plasmid according to claim 1, wherein said heterologous nucleotide sequence is inserted into the plasmid at a site other than the sequence of SEQ ID NO:1.

11. The modified plasmid according to claim 10, wherein said heterologous nucleotide is selected from the group consisting of a nucleic acid sequence which encodes a bacteriocin, a nucleic acid sequence which encodes a protein for immunity to a bacteriocin and a nucleic acid sequence which encodes a protein for resistance to an antibiotic.

12. The modified plasmid according to claim 10, wherein said heterologous nucleic acid sequence encodes a heterologous protein or peptide.

13. A host cell comprising a modified plasmid according to claim 11.

14. A modified plasmid obtained by inserting a heterologous nucleotide sequence into a plasmid according to claim 1, wherein said plasmid comprises the sequence of SEQ ID NO:2 and said heterologous nucleotide sequence is inserted into any site in the sequence of SEQ ID NO:2 apart from the sequence of SEQ ID NO:1.

15. The modified plasmid according to claim 14, wherein said heterologous nucleotide sequence is selected from the group consisting of a nucleic acid sequence which encodes a bacteriocin, a nucleic acid sequence which encodes a protein for immunity to a bacteriocin and a nucleic acid sequence which encodes a protein for resistance to an antibiotic.

16. The modified plasmid according to claim 14, wherein said heterologous nucleic acid sequence encodes a heterologous protein or peptide.

17. A host cell comprising a modified plasmid according to claim 15.

18. An isolated nucleic acid sequence comprising SEQ ID NO:1.

19. An isolated plasmid comprising the nucleotide sequence of SEQ ID NO: 1.

20. An isolated plasmid comprising the nucleotide sequence of SEQ ID NO:2.

21. A host cell comprising a plasmid containing the sequence of SEQ ID NO:1 and all or part of the sequence of SEQ ID NO:2 into which a heterologous nucleotide sequence is inserted.

22. *Leuconostoc mesenteroides* deposited in the National Collection of Microorganism Cultures on Oct. 30, 1997 under the number I-1936.

23. *Leuconostoc mesenteroides* deposited in the National Collection of Microorganism Cultures on Oct. 30, 1997 under the number I-1937.

24. A method for cloning a heterologous nucleic acid sequence comprising constructing a vector comprising SEQ ID NO:1 and a heterologous nucleic acid sequence.

25. A method for expressing a protein encoding by a heterologous nucleic acid sequence comprising:

a) constructing a vector comprising SEQ ID NO:1 and a heterologous nucleic acid sequence wherein said heterologous nucleic acid sequence is operably linked to a promoter;

b) transforming a host cell with said vector; and c) culturing said host cell to express said protein.

* * * * *

SEQUENCE LISTING

<160> NUMBER OF SEQ ID NOS: 4

<210> SEQ ID NO 1
<211> LENGTH: 1346
<212> TYPE: DNA
<213> ORGANISM: Leuconostoc mesenteroides

<400> SEQUENCE: 1

```
tcgacgttaa aagtttccat tctgtatctg tgaatgactt tttagataaa tctatattaa      60
ggcgtttagc tttctattta aggcttgacg tgatatttct agttcgtctg ctatcgcgat     120
aatggtatca aattcgtgtg tcatcagtct ctccaaacgt aaactgaagt gatgtaaagt     180
ttacgtttta agtttactat attgctgacg tttttaagtag gtcatttaat tattaaaaca    240
taagattatt tgtttgttta ttgtcatgta tagttcttaa tgctatactc atatcaacat    300
ttaaatacaa ataaaaagac ctcaactctt gcaggagtta ggacttggtg acctagatat    360
taacactatc agggttttgc cattacagaa ttcgacctct gaaatggctt agaatactta   420
ctattataca aacttataga ctaagagtaa acagctttac tcaaaaaaag aactataaac    480
gactatgaaa gcgtatcctc cagcctaact aagcacgagg atacgctttt tacgtctgtt    540
aagtcgttgt cggacgttat cctaacaact aatacggaac aggcgtgtat ccgtcaaagg    600
ggctgaaagg tcgcttaaac cacgtccaaa gatacaatag ctaacgtatc ggggaatgaa    660
caattcgatt atgggtaggc tcgcccgcaa gtgattggca aagaagtggc atatagagat    720
aagcgcctat atggtttaaa acgtctgtaa ggcgatttaa gcggtgtctg acgtgttcta    780
accttatgat aaggttttct attgggcaga cgatagaaaa gcaaatagag cgatatacgt    840
ggttgataca agcgatatga ttctgaatta taccttgaac aatttaaaaa gtcctaaata    900
cttagggctt cctctgctca aatcaaactg attgcccttg ttgattgtga tttacatttg    960
gtggtgttat tatgaaagcg tatatatttc tatatcatga tattttaatt cttttttaga   1020
aaggagtcta tctgtgacta tacttttttca agatgttcct gtttctgttt gggaaatcaa  1080
taagaatacc cctcagcccg attgggttaa aaactgtttt gaaaataata ctatggtttg   1140
gtatgacaat aggttaaaaa tacttgtaaa agctatcaat ccttctccaa aaagagatgt   1200
taaattaggt ttacgagata ccatgttagg ttattatggt ggtggatttg taatgggtaa   1260
tatcggtgat tattttgatg caacaaatgg acgtgttcta tcgaaaaaaa agttctataa   1320
```

-continued

```
gcaatacgtt ataaacgaat aatatt                                        1346

<210> SEQ ID NO 2
<211> LENGTH: 2665
<212> TYPE: DNA
<213> ORGANISM: Leuconostoc mesenteroides

<400> SEQUENCE: 2
tcgacgttaa aagtttccat tctgtatctg tgaatgactt tttagataaa tctatattaa      60
ggcgtttagc tttctattta aggcttgacg tgatatttct agttcgtctg ctatcgcgat     120
aatggtatca aattcgtgtg tcatcagtct ctccaaacgt aaactgaagt gatgtaaagt     180
ttacgtttta agtttactat attgctgacg ttttaagtag gtcatttaat tattaaaaca     240
taagattatt tgtttgttta ttgtcatgta tagttcttaa tgctatactc atatcaacat     300
ttaaatacaa ataaaaagac ctcaactctt gcaggagtta ggacttggtg acctagatat     360
taacactatc agggttttgc cattacagaa ttcgacctct gaaatggctt agaatactta     420
ctattataca aacttataga ctaagagtaa acagctttac tcaaaaaaag aactataaac     480
gactatgaaa gcgtatcctc cagcctaact aagcacgagg atacgctttt tacgtctgtt     540
aagtcgttgt cggacgttat cctaacaact aatacgaaac aggcgtgtat ccgtcaaagg     600
ggctgaaagg tcgcttaaac cacgtccaaa gatacaatag ctaacgtatc ggggaatgaa     660
caattcgatt atgggtaggc tcgcccgcaa gtgattggca aagaagtggc atatagagat     720
aagcgcctat atggtttaaa acgtctgtaa ggcgatttaa gcggtgtctg acgtgttcta     780
accttatgat aaggttttct attgggcaga cgatagaaaa gcaaatagag cgatatacgt     840
ggttgataca agcgatatga ttctgaatta taccttgaac aatttaaaaa gtcctaaata     900
cttagggctt cctctgctca aatcaaactg attgcccttg ttgattgtga tttacatttg     960
gtggtgttat tatgaaagcg tatatatttc tatatcatga tattttaatt cttttttaga    1020
aaggagtcta tctgtgacta tacttttttca agatgttcct gtttctgttt gggaaatcaa    1080
taagaatacc cctcagcccg attgggttaa aaactgtttt gaaaataata ctatggtttg    1140
gtatgacaat aggttaaaaa tacttgtaaa agctatcaat ccttctccaa aaagagatgt    1200
taaattaggt ttacgagata ccatgttagg ttattatggt ggtggatttg taatgggtaa    1260
tatcggtgat tattttgatg caacaaatgg acgtgttcta tcgaaaaaaa agttctataa    1320
gcaatacgtt ataaacgaat aatattaaat tatgacgttc tatattttg tctgatgagg    1380 aatgtgaaaa tgttgttgga gggcattggt tatcagatct tcttggtggg attgcacata    1440
catatcatcc tgctgacccc caaagagttc ttgaccaatt aaatgcaag actcaaccta    1500 aaccagggca tcaatgcagc ccttatggtt actattaaac attcagttaa cataagggtc    1560
attatacaaa gtaaaagcg ataaaccact tctagcaagg gttatcgct ttttgagtac    1620 caactagttt gtgaattcgt cttttttga ttggtctagc tggttaaacc ttggtttaat    1680
cacgttgcta gtttgtgaaa tgactagatt ttaagcacgc tttttctgg atacttgtaa    1740 gaatatcaga tatgaagccg taaaaactac aaagtagaca acatcaaacc aaaatgatgt    1800
acttaatgta ccaccgtcta acagttgaaa cacaatatca atagcacacc aaccagcaat    1860
agttatccct atgctaatca ttaatttaac gaaccaattc attagtaatc gccctctgtt    1920
tctattgtat caacaaccaa cattgttgag tagctaaatt ggtatctaat ctaattatac    1980
taataagcaa aataatccgt cagcaaaacg acataaaatg agtttaatgc gcacttacac    2040
```

-continued

```
atcactttt  caagtgatga  aattgcttga  acattttatc  agaatgcgca  cttacacacc  2100
acacataaat  tggtggtggt  attgcccaaa  aaaattgtgt  cagaagtcgc  ttatagcgac  2160
aacttaaaaa  ccaacaaaag  ttcttgttgc  gagcatacta  agtgggtacc  cacttagggt  2220
aaaaactaat  catctgacga  gctaaacaac  ctaaaatgta  attttagatt  gccgctcttt  2280
cagatgatta  gttttttgttt  tgggggtttc  ccaatcccct  ttttgaattaa  aattaattttt  2340 gataagcgga  cggttgatga  acgaaaaata  ctaacaaaca  aaacggacgc  tataaaatta  2400
cctttgaaaa  actatttaaa  taatctatgc  cagaatcctt  tctttggctg  attttctttt  2460
tcttgatact  caattagggt  tttatttgtc  tctgttaatc  tttgttcagc  aattaattgc  2520
aattgttgcg  catgatcaat  ttgtttatct  ttttctttaa  tttgcgattt  taaataatta  2580
attaaatcat  cttttttcagc  tagttgttgc  gctgtaaaag  tgtcaacata  gttacttgaa  2640
gttgactgtt  ttggtttacg  tttag                                            2665
```

<210> SEQ ID NO 3
<211> LENGTH: 80
<212> TYPE: PRT
<213> ORGANISM: Leuconostoc mesenteroides

<400> SEQUENCE: 3

```
Arg Ile Pro Ser His Val Ile Arg Asn His Thr Pro Glu Gly Ala Leu
1               5                   10                  15

Ser Gln Cys Leu Leu Pro Met Tyr Leu Tyr Ala Gly Ile His Asn Leu
            20                  25                  30

Val Asp Thr Leu Arg Asn Leu Arg His Arg Val His Glu Leu Arg Ile
        35                  40                  45

Ile Leu Asn Glu Ile Pro Cys Val Ile Ser Phe Cys Ile Ser Arg Tyr
    50                  55                  60

Val His Asn Ile Cys Ala Ile His Asn Gln Ile Ile Gly Gln Val Ile
65                  70                  75                  80
```

<210> SEQ ID NO 4
<211> LENGTH: 113
<212> TYPE: PRT
<213> ORGANISM: Leuconostoc mesenteroides

<400> SEQUENCE: 4

```
Tyr Phe Asn Ser Phe Leu Glu Arg Ser Leu Ser Val Thr Ile Leu Phe
1               5                   10                  15

Gln Asp Val Pro Val Ser Val Trp Glu Ile Asn Lys Asn Thr Pro Gln
            20                  25                  30

Pro Asp Trp Val Lys Asn Cys Phe Glu Asn Asn Thr Met Val Trp Tyr
        35                  40                  45

Asp Asn Arg Leu Lys Ile Leu Val Lys Ala Ile Asn Pro Ser Pro Lys
    50                  55                  60

Arg Asp Val Lys Leu Gly Leu Arg Asp Thr Met Leu Gly Tyr Tyr Gly
65                  70                  75                  80

Gly Gly Phe Val Met Gly Asn Ile Gly Asp Tyr Phe Asp Ala Thr Asn
            85                  90                  95

Gly Arg Val Leu Ser Lys Lys Phe Tyr Lys Gln Val Val Ile Asn
        100                 105                 110

Glu
```